United States Patent
Fabian et al.

(10) Patent No.: US 9,282,890 B2
(45) Date of Patent: Mar. 15, 2016

(54) EYE IMAGING APPARATUS

(71) Applicant: William Fabian, Washington, DC (US)

(72) Inventors: William Fabian, Washington, DC (US); Timothy White, New Boston, NH (US)

(73) Assignee: William Fabian, Hutchinson, KS (US)

( * ) Notice: Subject to any disclaimer, the term of this patent is extended or adjusted under 35 U.S.C. 154(b) by 0 days.

(21) Appl. No.: 14/217,668

(22) Filed: Mar. 18, 2014

(65) Prior Publication Data

US 2014/0268053 A1     Sep. 18, 2014

Related U.S. Application Data

(60) Provisional application No. 61/793,002, filed on Mar. 15, 2013.

(51) Int. Cl.
| | | |
|---|---|---|
| A61B 3/14 | (2006.01) |
| A61B 3/00 | (2006.01) |
| A61B 3/10 | (2006.01) |
| A61B 3/15 | (2006.01) |
| A61B 5/00 | (2006.01) |
| A61B 3/11 | (2006.01) |
| A61B 5/11 | (2006.01) |

(52) U.S. Cl.
CPC ............. *A61B 3/152* (2013.01); *A61B 3/156* (2013.01); *A61B 5/4519* (2013.01); *A61B 3/112* (2013.01); *A61B 3/145* (2013.01); *A61B 3/154* (2013.01); *A61B 5/1104* (2013.01)

(58) Field of Classification Search
CPC ........... G02B 27/0172; G02B 27/0149; G02B 27/145; G02B 27/143; G02B 27/0025; G02B 27/144; G02B 27/1013; G02B 23/02; G02B 23/18; G02B 5/045; G02B 27/0103; G02B 17/08; A61B 3/103; A61B 3/152; A61B 3/14; A61B 3/113; A61B 3/1225
USPC ................. 351/208, 200, 205–206, 210, 221; 359/630–639, 404, 407, 409–410, 359/618–619, 625, 13–14, 727, 732; 345/7, 345/9; 349/11; 353/11–12, 28, 119; 348/115; 340/438, 980, 995.1, 815.47, 340/815.74
See application file for complete search history.

(56) References Cited

U.S. PATENT DOCUMENTS

| | | | |
|---|---|---|---|
| 5,345,281 A * | 9/1994 | Taboada et al. | 351/210 |
| 7,146,983 B1 * | 12/2006 | Hohla et al. | 128/898 |
| 8,323,216 B2 | 12/2012 | Fabian | |
| 2002/0085843 A1 * | 7/2002 | Mann | 396/374 |
| 2005/0110949 A1 * | 5/2005 | Goldfain et al. | 351/206 |
| 2010/0128221 A1 * | 5/2010 | Muller et al. | 351/207 |

* cited by examiner

*Primary Examiner* — Dawayne A Pinkney
(74) *Attorney, Agent, or Firm* — Duane Morris LLP

(57) ABSTRACT

An optical device combination with a portable electronic device utilizes a user's autonomic response to truth/false or beneficial/non-beneficial stimulus and provides immediate feedback to the user in the context of an applied kinesiology exam. Through measurements of the pupils dilation or constriction and processing of the measurements by the portable electronic device, the response is obtained and feedback is provided that reflects the pupillary response. The device and method effectively eliminate the subjective components of prior art muscle testing response from the hands of the testing user as well as providing a simple convenient and portable attachment to a user's smart phone.

20 Claims, 4 Drawing Sheets

EYE IMAGING APPARATUS

CROSS REFERENCES

This application is a non-provisional application and claims priority benefit of provisional application Ser. No. 61/793,002 entitled "Eye Imaging Apparatus" filed 15 Mar. 2013. The entirety of which is hereby incorporated by reference.

BACKGROUND

The background of applied kinesiology (AK) in general dates back to George Goodhart, D. C. (1964) in which the observation that the gross, striated muscle response is one of going weak to a detrimental stimulus and remaining strong to a beneficial stimulus was made.

Applied kinesiology interactive assessment procedures represent a form of functional biomechanical and functional neurologic evaluation. The term "functional biomechanics" refers to the clinical assessment of posture, organized motion such as in gait, and ranges of motion. Muscle testing readily enters into the assessment of postural distortion, gait impairment and altered range of motion. During a functional neurologic evaluation, muscle tests are used to monitor the physiologic response to a physical, chemical or mental stimulus. The observed response is correlated with clinical history and physical exam findings and, as indicated, with laboratory tests and any other appropriate standard diagnostic methods.

The applied kinesiology response has been used by chiropractors since the mid 20th Century for diagnostic purposes. In the past, the muscle response measure was achieved through gross physical movements of voluntary muscle groups.

An example of a prior art kinesiology exam in FIG. 4 is taken from David Hawkins' "Power versus Force" 1995, Veritas Publishing page 3, excerpted from H. O. Kendall's *Muscles: Testing and function* (Baltimore: Williams and Wilkins, second edition, 1971).

It typically takes two people to perform a kinesiological test. One is a friend or family member for testing. We'll call him or her, your subject, and you will be the examiner. Have the subject standing erect, right hand relaxed at subject's side, left arm held out parallel to the floor, elbow straight (Block 401). (You may use the other arm if you wish). Face your subject and place your left hand on his right shoulder to steady him. Then place your right hand on the subject's extended left arm just above the wrist (Block 403). Inform the subject you're going to try to push his arm down as he resists (Block 405). Now push down on his arm fairly quickly, firmly and evenly (Block 407). The idea is to push just hard enough to test this spring and balance in the arm but not so hard that the muscle becomes fatigued. The phenomenon is not a question of who is stronger, but of whether the muscle can "lock" the shoulder joint against the push. You then determine the resistance (Block 409) and determine whether it is strong or weak (Block 411).

Assuming there is no physical problem with the muscle and the subject is in a normal and relaxed state of mind, receiving no extraneous stimuli (for this reason it is important that the examiner not smile or otherwise interact with the subject), the muscle will "test strong"—that is the arm will remain locked or have a high resistance (Block 413). If the test is repeated in the presence of a negative stimulus (for instance, artificial sweetener), although you are pushing down no harder than before, the muscle will not be able to resist the pressure and the subject's arm will fall to his side (Block 415).

The same is the case for muscle responses to statements that are true and not true: the muscle staying strong under "true" conditions and going weak under "not true" conditions, (i.e., a false statement). Likewise, it has been reported by Davis, C. 2007 (in Hawkins, D. 2008 "Reality, Spirituality, and Modern Man) that the pupil dilates to false and constricts to true statements made by the individual. This smooth muscle, autonomic activity, provides a unique way of assessing the naturally occurring applied kinesiology response.

Goodhart (1976) also noted a response in individuals listening to statements of deceit; that is, large striated muscle tested weak in the presence of statements known to be false, such as the tape recordings of Lyndon Johnson talking about the "Tonkin gulf" or Edward Kennedy stonewalling on Chappaquiddick. These parsimonious observations by Goodhart carry implications for national security interests in that the false information is not being expressed by the individual tested (i.e., the person being tested isn't doing the lying), but the false information is being detected by the person listening to it. This particular phenomenon is described and explained by Hawkins as a "field effect". The theoretical explanation is in terms of quantum physics, "nonlocal effects", and hence somewhat "edgy" to the everyday understanding, but the observable functionality is what is remarkable and holds tremendous promise if the parameters by which it works are validated. In other words, because of the field effect of a false statement, one does not have to be present at the location to detect it.

U.S. Pat. No. 8,323,216, describes the general methodology of objectively assessing the naturally occurring applied kinesiology response. The entirety of which is herein incorporated by reference.

The present subject matter provides an improved device for measuring characteristics of at least one eye, and particularly for measuring the physiological changes in the eyes under different conditions of truthfulness (beneficial) and falseness (non-beneficial).

The present subject matter also removes the subjective components of the muscle testing response from the testing individual by automatically monitoring an involuntary (autonomic) pupillary response using an automated process.

The present subject matter provides a device connectable to a smart phone, or other portable processor. The combination of the device and smart phone simplifies the administration and results analysis of an applied kinesiology examination.

In addition the present subject matter eliminates the deleterious effects of glare associated with prior art imaging of the eye.

These and many other aspects and advantages of the present subject matter will be readily apparent to one skilled in the art to which the invention pertains from a perusal of the claims, the appended drawings, and the following detailed description of preferred embodiments.

DETAILED DESCRIPTION

The disclosed optical attachment (interchangeably referred to as an optical device) is a device that attaches to a smart phone or other portable electronic device that documents the phenomenon of the iris's response to truthfulness versus falseness (as well as beneficial versus non-beneficial conditions) and that gives immediate feedback to the individual. The optical device and smart phone collectively referred to as the imaging apparatus advantageously takes the subjective components of the muscle testing response out of the hands of the testing individual and monitors an involuntary (autonomic) pupillary response, using a computationally derived function effectively eliminating a subjective component to the muscle testing process while requiring only one individual be involved. The optical device may be a personalized, self-contained mechanism whereby an individual working solely by themselves can ascertain the results of the applied kinesiology response. In other words, an individual may obtain the truthfulness of a statement without the presence of a second person. Previous applied kinesiology responses required two individuals; an examiner and a subject. This device allows for self-evaluation and eliminates a subjective influence on obtaining the response between two people.

Real-time observation and measurement of the dynamic geometry of the iris and pupil is of great value for various applications involving autonomic nervous system responses to various stimuli. Moreover, the optical device enables first hand observation of the eye while imaging takes place. For example, dilation of the pupil is correlated with the telling of a lie. Prior art devices involve elaborate and expensive apparatuses for obtaining the desired images of the eye. The disclosed subject matter makes use of a simple and inexpensive optics and light source mounted on a smart phone to acquire, process and record images of the iris and pupil in real time in order to observe autonomic nervous system responses to various stimuli. Measurement of the iris is improved by measuring both the iris and pupil diameter, and expressing the pupil diameter and iris diameter in many different functions such as a fraction of the pupil diameter over the iris diameter rather than as an absolute measurement, such relational measurement being immune to apparent dimensional changes caused by slight changes in the distance from the eye to the optics. Other functions such as area relationships are also envisioned.

Figure 1:
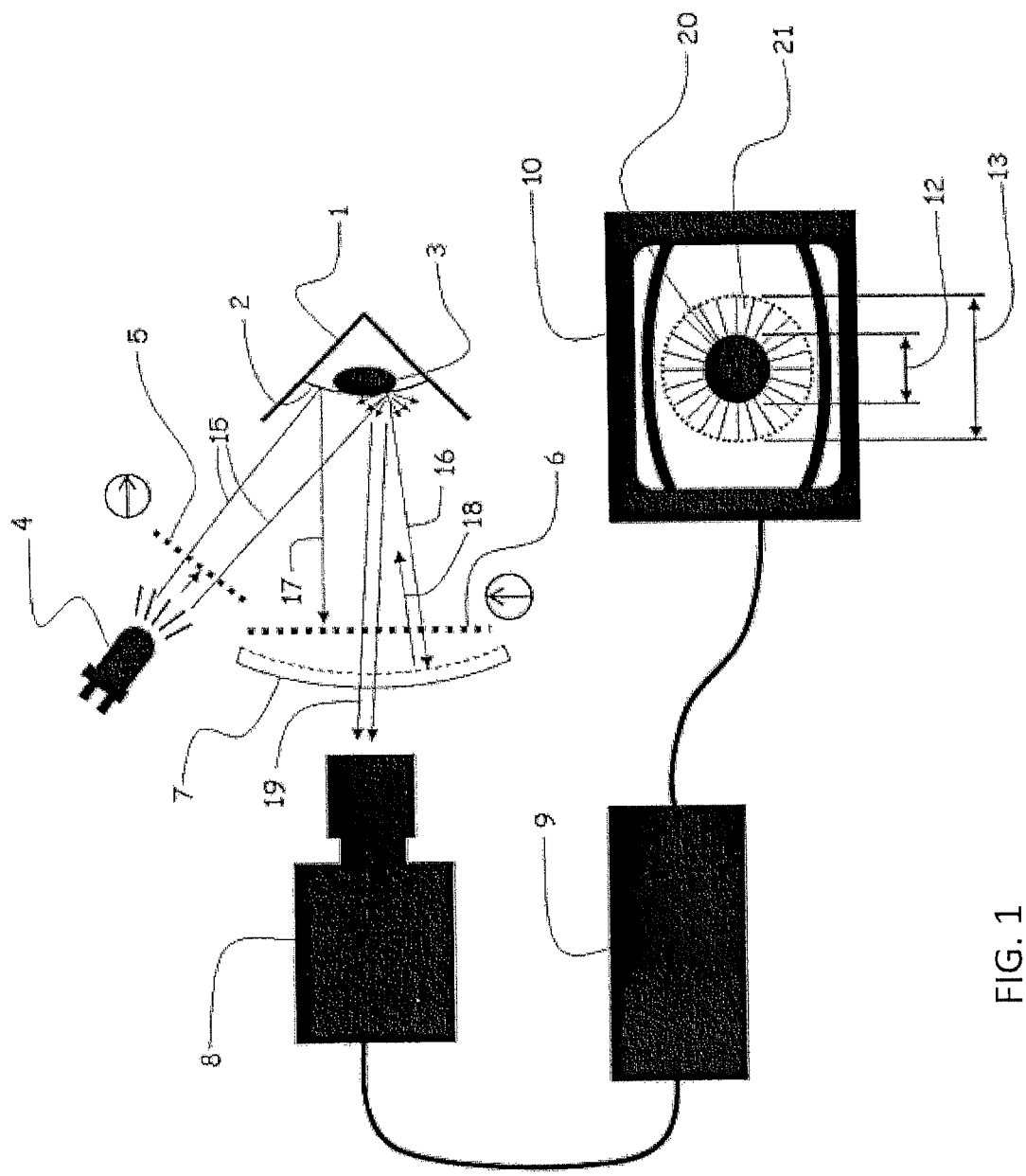
FIG. 1 is a schematic of an imaging system according to an embodiment of the present subject matter.

In FIG. 1 the observer's eye 1 is shown schematically in plain view. Illumination from light source 4 is p-polarized by polarizing filter 5. P-polarized light 15 passing through the p-polarizing filter 5 is reflected specularly off the surface of the cornea 2 and diffusely off of the iris tissue 3. Specularly reflected rays 17 maintain their p-polarization and are blocked by the n-polarizing analyzer filter 6. Diffusely reflected rays 16 and 19 lose their polarization and pass through the n-polarizing analyzer filter 6 to the half-silvered mirror 7 where they are either reflected back to the eye 18 for observation, or pass 19 through the beamsplitter 7 to the camera 8. The images from the camera 8 are processed in image processor 9 and displayed on video display 10. Pupil 20 diameter measurement 12 and iris 21 diameter measurement 13 are obtained via a measurement algorithms. The measurements are reported either directly, or as a ratio, or in some other manner.

The imaging apparatus allows the user to view a reflection of their own eye at high magnification while simultaneously obtaining a video image of the eye. Illumination artifacts are attenuated via cross-polarized light filters on the light source and video camera lens aperture. The half-silvered mirror allows the video camera to view the eye coaxially without the camera being seen by the eye directly. An image processor allows measurements to be made of eye features such as the pupil and iris as discussed above. An algorithm which measures the iris diameter as a fraction of the pupil diameter, rather than as an absolute measurement, eliminates measurement variance due to variations in distance between the eye and the imaging apparatus. The optical device may advantageously be mounted removably on the smart phone making use of the smart phone's camera and processor to perform the desired image analysis. The algorithm may be downloaded to the smart phone in a conventional manner.

Figure 2:
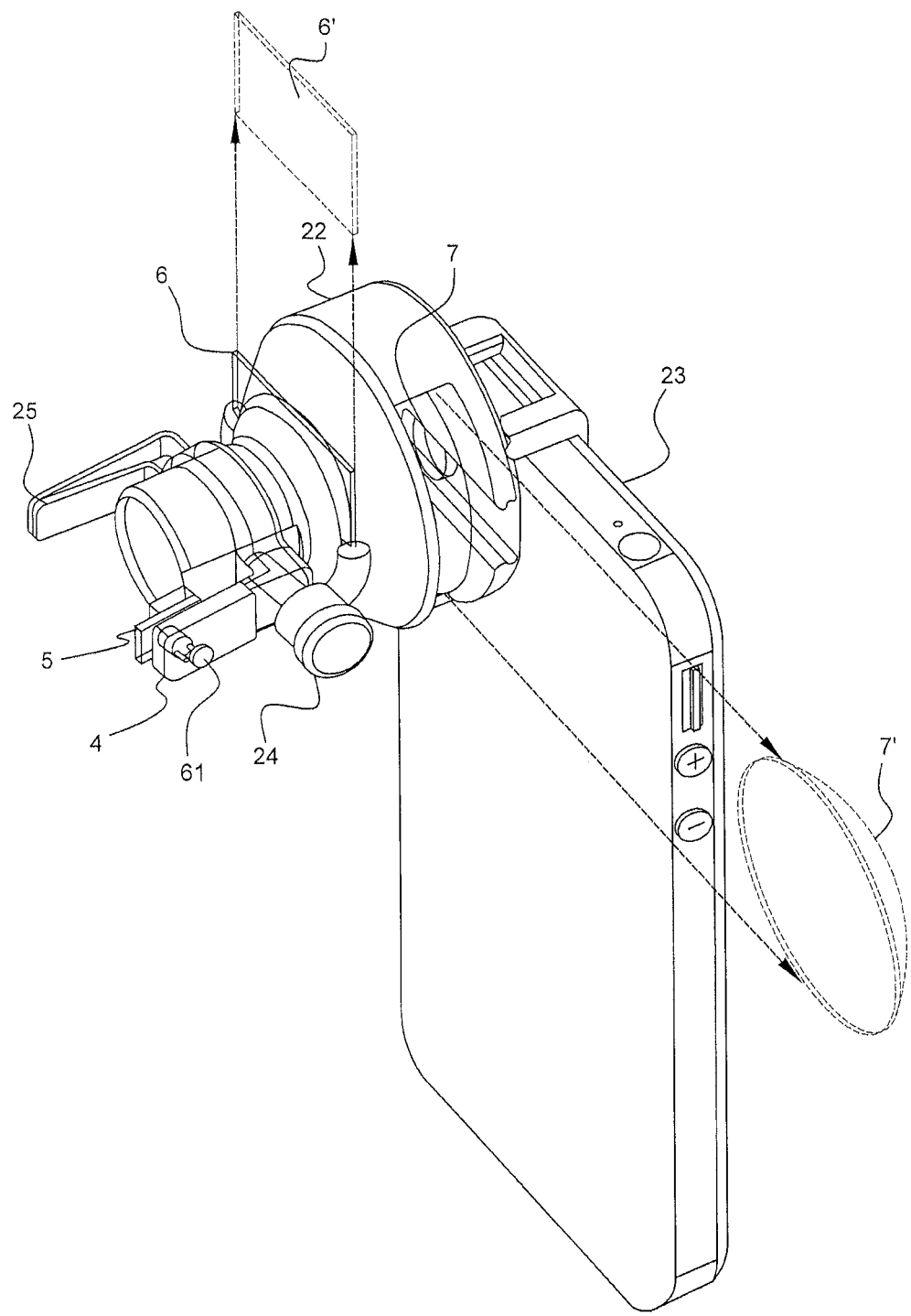
FIG. 2 is a isometric view of an optical device attached to a portable electronic device according to an embodiment of the present subject matter.

FIG. 2 shows an implementation of an embodiment of the present subject matter. The representative optical device 22 is shown removably attached to a smart phone 23. In one embodiment, the light source LED 4 and p-polarizer 5 are shown mounted on an adjustable slide 24 which allows the distance and angle of the light source 4 to be optimized for each user. The n-polarizing analyzer filter 6 and reflecting beam splitter 7 are shown removably inserted into the assembly 22 as 6' and 7'. In this embodiment, a mirror 25 reflects light from the light source 4 and reflects it from an opposite angle, thereby creating a more uniform illumination geometry.

Figure 3:
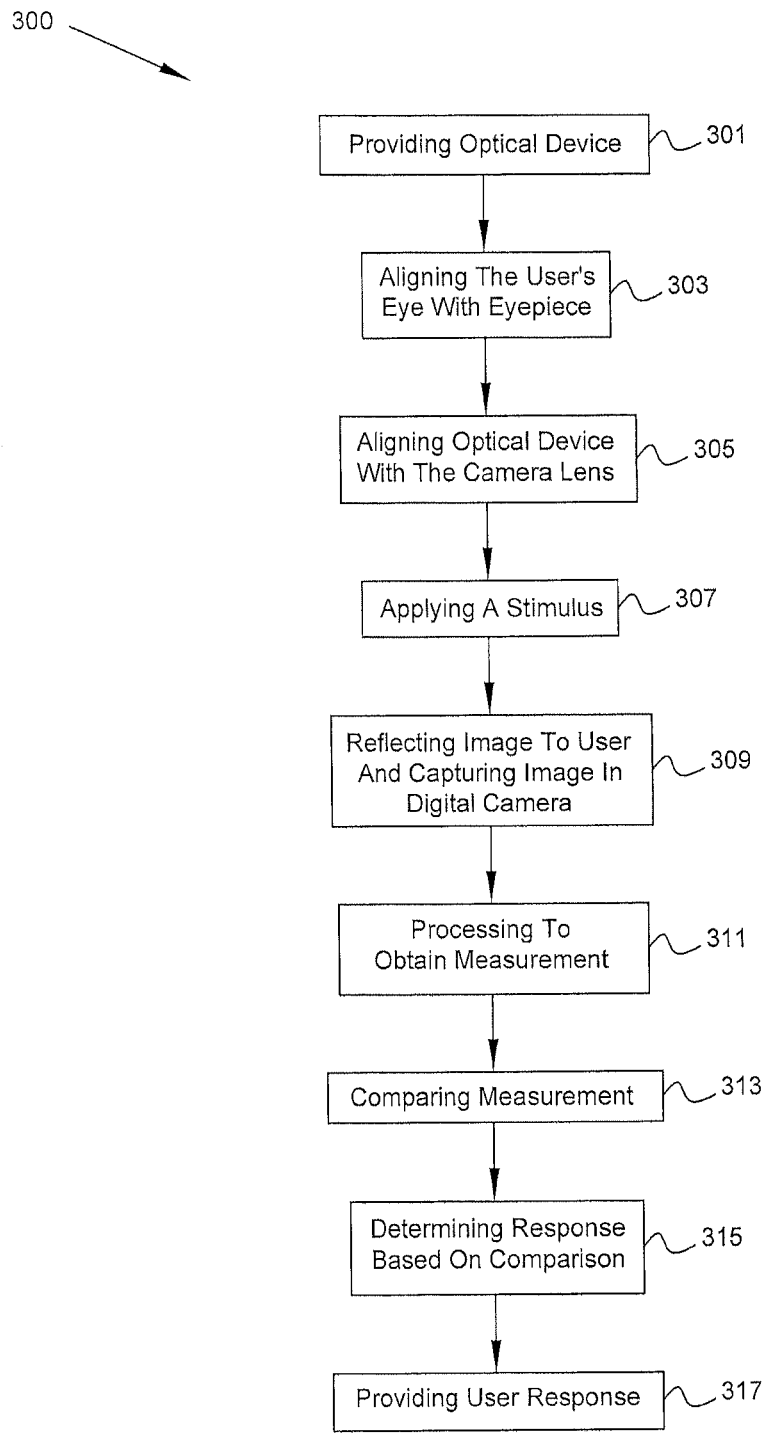
FIG. 3 is a flow diagram for a method of measuring the user's response to a stimulus according to an embodiment of the present subject matter.
Figure 4:
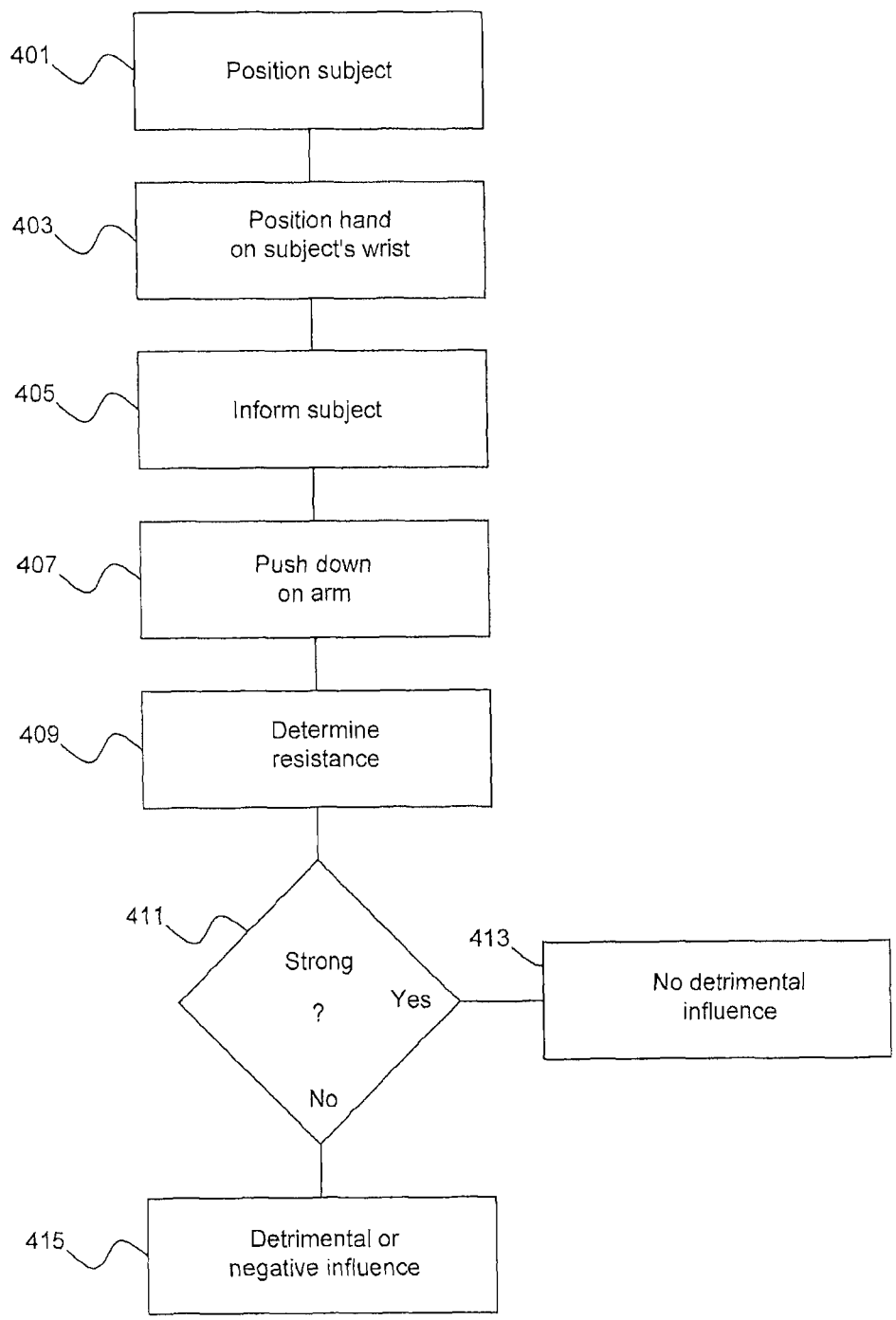
FIG. 4 is a flow diagram of a prior art kinesiology examination.

FIG. 3 illustrates a method 300 of measuring the response of a user's eye to a stimulus. As shown in Block 301, the optical device with an eye piece end and a camera end is provided. The eye piece end is aligned with the user's eye as shown in Block 303 and the camera end is aligned with the lens of a smart phones digital camera as shown in Block 305, this alignment may be seen in FIG. 2. A stimulus is then applied to the user as shown in Block 307 and an image of the user's eye is captured with the digital camera while simultaneously reflecting the image through the eye piece end to the user's eye both contemporaneous with the application of a stimulus as shown in Block 309. The captured image is processed in the smart phone to obtain a measurement of a characteristic of the user's eye as shown in Block 311 and this measurement is compared with a predetermined measurement to determine the user's response as shown in Blocks 313 and 315. An indication of the user's response is then provided to the user via the smart phone as shown in Block 317. The indication of response may be a visual signal including illuminating a light having a predetermined color to the subject, illuminating a light with a predetermined brightness to the subject, pulsing a blinking light at a predetermined frequency, or pulsing a light a predetermined number of pulses or combination thereof. The indication may also be an aural signal such as a synthesized voice, a recorded voice, a tone, a volume or a number of audio pulses. The indication may also be a non-audible vibration or other sensory stimulant.

The method for determining the autonomic response may be practiced using a control stimulus and an active (or response) stimulus. The control stimulus establishes a base line or normative value and expected deviations of the property characteristic (pupil dilation). The active or response establishes the autonomic response temporal to the stimulus. The process is advantageously performed first using a control stimulus to obtain control measurements such that, the processor may determine the baseline of the pupil diameter or baseline function. Subsequent characteristics of the pupil may be measured and the resultant increase/decrease/steady state of the pupil characteristic is used by the smart phone to determine the user's response to the stimulus.

An advantage of the optical attachment/device is to provide a simple and unique means of delivering feedback on the applied kinesiology response of the pupil. The optical device along with the portable electronic device to which it is attached provide visual or other form of feedback of a true versus not true response to a particular statement or stimulus. The indication may be in the form of a tone, voice, a display of color, a display of text, a display of an image or vibration by the portable electronic device.

Yet another aspect of the present subject matter is it allows the individual to test themselves for diagnostic purposes (eliminating the need for another practitioner) and allows diagnostic processes to be done on other individuals without them being present. This allows for portability, convenience, and eliminates subjectivity that may be involved with an additional individual. In addition to the diagnostic implications, the optical device represent a step forward in the ability and means to make assessment decisions (true versus false) in a remote manner. Implications for the disclosed subject matter are far-reaching including medical assessment and diagnosis, lie detection, armed service conditioning, gaming and remote/distant knowledge gathering through a convenient and non-intrusive, and individualized, method and apparatus.

Aspects of the disclosed subject matter may be specifically implemented by algorithms embedded in software provided on the electronic device which may be in the form of an "app". Another aspect of the disclosed subject matter is that the optical attachment may be integrated into a portable electronic device, rather than being an accessory.

Portable electronic devices envisioned include laptops, personal digital assistants, notebook computers, tablets, digital cameras and other devices with a digital camera capability along with processor capability. For purposes of the disclosure a smart phone is used as an example in describing the invention, however such use is not intended to be limiting as a broad range of portable electronic devices are contemplated.

An advantage of the present subject matter as described herein allows users to simultaneously view a reflection of their eye while also capturing an image of the eye. This allows the user to ensure the eye is positioned properly with respect to the device and may allow the users to validate the results from the processor. The beam splitter may be marked with indications such as a cross hair allowing the user to properly position his eye in the reflection, as may the analyzer filter. Additional markings on the beam splitter or filter may allow the user to access changes in the pupil dilation based on the coincidence of the pupil with the marks. While the polarization discussed in the present disclosure is p and n polarization, other polarizations, polarization combinations and filters may also be used. In addition, any number of optical components may be substituted to capture and reflect the image, and thus the use of lenses, mirrors, prisms, edges, pin holes, etc. can be assembled by one skilled in the art to perform the steps described of the disclosed subject matter.

In instances where a processor may not be accessible or available on the digital camera, the images may be recorded, time stamped and stored for later review.

While preferred embodiments of the present invention have been described, it is to be understood that the embodiments described are illustrative only and that the scope of the invention is to be defined solely by the appended claims when accorded a full range of equivalence, many variations and modifications naturally occurring to those of skill in the art from a perusal hereof.

The invention claimed is:

1. An imaging system for capturing images of a user's eye, comprising:
   a light source, said light source positioned to illuminate the iris of the user's eye;
   a first polarizing filter, said first polarizing filter positioned between the light source and the user's eye and emits light with a first polarization;
   an analyzer filter, said analyzer filter blocking light with the first polarization;
   a partial light reflector, said light reflector disposed proximate and substantially normal to an optical axis of the user's eye, said partial light reflector positioned to reflect a mirror image of the user's eye towards the user's eye;
   an image recorder, said image recorder positioned to capture images of the user's iris;
   an image processor connected to the image recorder; and
   a display unit, said display unit operable connected to the image processor.

2. The imaging system, according to claim 1, further comprising a plurality of reference marks observable by the user on the analyzer filter or the partial light reflector, wherein the reference marks indicate alignment position or relative diameter.

3. The imaging system according to claim 1, wherein the light source is a fiber optic light guide.

4. The imaging system, according to claim 1, wherein the analyzer filter, whose plane of polarization is substantially perpendicular to that of the polarization of light reflecting off of the observed eye's surface, is disposed between the observed eye and the light reflecting means.

5. The imaging system, according to claim 3, where the light reflector is a partially reflective beam splitter.

6. The imaging system, according to claim 5, where the partially reflective beam splitter forms an image magnifying curved reflective surface as viewed by the user's eye.

7. The imaging system, according to claim 1, where the imaging recorder and processor and display are comprised of a smart phone.

8. A optical device configured to attach to a portable electronic device for observing and capturing an image of the user's eye, comprising:
   a housing having a first end with a first opening and a second end with a second opening;
   a light passage;
   a light source positioned proximate to the first end;
   a polarizing filter positioned to receive light emitted from the light source and provide light to the user's eye with a first polarization;
   an analyzing filter intersecting the light passage, the analyzing filter blocking light with a first polarization from passing;
   a beam splitter, said beam splitter projects a portion of the light incident upon it through the second opening and a mirror image of the user's eye thru the first opening to the user's eye; and,
   a clip configured to removably attach the optical device to the portable electronic device and to align the second opening with a lens of a digital camera when the optical device is attached to the portable electronic device;
   wherein the light passage extends from the first opening through the analyzing filter, the beam splitter and the second opening, wherein the beam splitter is co-axial with the light passage.

9. The optical device at claim 8, further comprising a mirror disposed opposite of the light source proximate the first end of the housing.

10. The optical device of claim 8, further comprising a slide and wherein the slide adjusts the distance between the first end and the viewer's eye.

11. The optical device of claim 8, wherein the housing further comprises a slot to removably receive the analyzer filter.

12. The optical device of claim 8, wherein the housing further comprises a slot to removable receive the beam splitter.

13. The optical device of claim 8, wherein the beam splitter is co-axial with the light passage.

14. A method of measuring the response of a user's eye to a stimulus, comprising:
  a. providing an optical device having a first end and a second end;
  b. aligning the first end to the user's eye;
  c. aligning the second end to a digital camera associated with a portable electronic device;
  d. applying a stimulus to the user;
  e. recording an image of the user's eye with the digital camera and reflecting a mirror image of the user's eye through the first end to the user's eye contemporaneous with the application of a stimulus; wherein the recording and reflecting are performed simultaneously;
  f. processing the captured image to obtain a measurement of a characteristic of the user's eye, wherein the processing is by a processor in the portable electronic device;
  g. comparing the measurement with a predetermined measurement in the processor;
  h. determining the user's response in the processor based on the comparison; and,
  i. providing an indication of the user's response to the user via the portable electronic device.

15. The method of claim 14, wherein the step of capturing an image of the user's eye with the digital camera further comprises:
  i. illuminating the users' eye;
  ii. filtering light reflected from the user's eye based on a first polarization;
  iii. reflecting back to the user's eye a portion of the filtered light; and,
  iv. directing another portion of the passed light to the digital camera.

16. The method of claim 14, wherein the predetermined measurement is determined by:
  j. applying a control stimulus to the user;
  k. capturing a first image of the user's eye with the digital camera contemporaneous with the application of the control stimulus; and,
  l. processing the captured first image to obtain a first measurement of a characteristic of the user's eye.

17. The method of claim 16, where in the step of capturing the first image comprises:
  i. illuminating the users' eye;
  ii. filtering light reflected from the user's eye based on a first polarization;
  iii. reflecting back to the user's eye a portion of the filtered light; and,
  iv. directing another portion of the passed light to the digital camera.

18. The method of claim 16, wherein the step of illuminating the user's eye comprises providing a light source and polarizing the light with the first polarization.

19. The method of claim 14, wherein the optical device comprises:
  a polarizing filter; an analyzing filter; a beam splitter; and a clip.

20. The method of claim 14, wherein the characteristic is pupil diameter.

* * * * *